United States Patent [19]

Tunc

[11] Patent Number: 4,623,539
[45] Date of Patent: * Nov. 18, 1986

[54] NUTRIENT BARRIER POLYSACCHARIDE COMPOSITIONS AND METHOD OF USE

[76] Inventor: Deger C. Tunc, 6 Springfield Rd., East Brunswick, N.J. 08816

[*] Notice: The portion of the term of this patent subsequent to May 28, 2002 has been disclaimed.

[21] Appl. No.: 716,473

[22] Filed: Mar. 25, 1985

Related U.S. Application Data

[62] Division of Ser. No. 464,024, Feb. 4, 1983, Pat. No. 4,520,017.

[51] Int. Cl.$^4$ .................. A61K 31/72; A61K 31/725; C08B 37/00; C08B 37/08
[52] U.S. Cl. ........................................ 424/79; 424/80; 514/54; 514/55; 514/56; 514/57; 514/23
[58] Field of Search ................... 536/118, 121, 20, 21; 514/54, 55, 56, 57, 492, 494, 461; 424/79, 80

[56] References Cited

U.S. PATENT DOCUMENTS

| | | | |
|---|---|---|---|
| 2,572,923 | 10/1951 | Gaver et al. | 536/121 |
| 2,697,093 | 12/1954 | Jones | 536/118 |
| 3,510,561 | 5/1970 | Koh | 514/56 |
| 3,632,754 | 1/1972 | Balassa | 514/55 |
| 4,021,544 | 5/1977 | Nair et al. | 536/118 |
| 4,389,523 | 6/1983 | Okajima et al. | 536/118 |
| 4,443,486 | 4/1984 | Guiseley | 536/118 |
| 4,520,017 | 5/1985 | Tunc | 514/57 |
| 4,524,066 | 6/1985 | Wolf | 536/118 |

*Primary Examiner*—Johnnie R. Brown

[57] ABSTRACT

Disclosed are method and composition for periodically coating the internal, food absorbing surface of the small intestine of a mammal by ingesting said composition which is capable of forming at least a partial nutrient barrier on said intestine.

22 Claims, No Drawings

NUTRIENT BARRIER POLYSACCHARIDE COMPOSITIONS AND METHOD OF USE

This application is a division of my copending application Ser. No. 464,024, filed Feb. 4, 1983, issued as U.S. Pat. No. 4,520,017, on May 28, 1985.

FIELD OF THE INVENTION

This invention relates to the field of weight control. More particularly, it relates to a method of periodically coating the internal, food absorbing surface of the small intestine by ingesting a composition which is capable of forming at least a partial nutrient barrier on said intestine. The composition of the invention is ingested prior to or along with regular meals effecting no significant changes in the eating habit of the individual.

BACKGROUND OF THE INVENTION

Obesity has become a special concern in recent years for the medical profession. A substantial portion of the U.S. population weighs more than the medically indicated ideal body weight and risks an increased incidence of various diseases associated with overweight, such as hypertension, diabetes, and circulatory diseases.

To control obesity, various methods are being used. Appetite depressants, for example, constitute a large portion of the anti-obesity regimen. These drugs work on the central nervous system and while depressing the appetite the also slow down and undesirably effect other functions of the body.

Another approach to achieve weight reduction is the jejunoileal by-pass operation which shortens the intestine available for nutrient absorption. Notwithstanding the operation's beneficial effect initially, it was observed that the body adapts to the shortened intestine and the patient tends to regain the weight lost initially.

Among the other weight reduction methods are the various diets with various degrees of success. The disadvantages of these methods are twofold: a lack of balanced diet resulting in malnutrition, and a requirement of changing the eating habits of individuals which in many cases cannot be maintained over a sufficiently long period of time to attain weight reduction.

There is obviously a need to provide an obesity control regimen which will not adversely effect any of the normal body functions and which will not necessitate a change in the eating habits of individuals.

Broadly defined, the nutritive process includes digestion, absorption and metabolism. This process is the sum total of the physical and chemical activities that take place within the cells and the relationships that exist between the cells and the surrounding environment.

Digestion includes the mechanical and chemical processes whereby food materials are transformed to forms that are suitable in consistency and composition for absorption into the mucosal wall and for utilization by the body. The gastrointestinal tract controls the amounts of certain substances that will be absorbed, prevents the absorption of unwanted molecules, synthesizes enzymes and hormones that are required for the digestive process, and eliminates the wastes remaining after the digestion of the food. The gastrointestinal tract is about 25 to 30 feet long in the adult and includes mouth, esophagus, stomach, small intestine (duodenum, jejunum and ileum), and large intestine (edum, colon, rectum and anal canal).

The rate at which foods move through the digestive tract depends upon the consistency, composition and amount of food intake. Liquids begin to leave the stomach from 15 minutes after ingestion; carbohydrates leave the stomach faster than do proteins; and fats are even slower to leave than proteins. A large complex meal takes about nine hours to pass from the small intestine into the large intestine. After consumption of a meal, typically 20 to 36 hours are required to eliminate food residues from the body.

The process whereby nutrients move from the intestinal lumen into the blood or lymph circulation is known as absorption and results in a net gain of nutrients to the body. Absorption requires that the nutrients penetrate the cell wall, cross the cell, exit from the cell into the lamina propria, and cross the epithelium of the blood or lymph vessels. Absorption appears to take place primarily from the duodenum and jejunum. (A notable exception is Vitamin $B_{12}$, which has a specific absorption site in the lower ileum.) Normally, 98% of the carbohydrate, 5% of the fat and 92% of the protein in the diet is hydrolyzed and the end products are absorbed. The small intestine provides an absorbing surface that is about 600 times as great as its external surface area. This is possible because of the arrangement of the mucosal wall in numerous folds, the four to five million villi that constitute the mucosal lining, and the five hundred to six hundred microvilli that form the "brush border" of each epithelial cell of the villus. The mechanism of absorption is described in more detail, for example, in *Normal and Therapeutic Nutrition,* 14th Edition by C. H. Robinson, Collier-MacMillan Limited, London, 1972, pp. 1–28.

The control of the absorption process of nutrients through the digestive tract has been investigated in recent years. For example, in the article entitled, "Avian Atherosclerosis: Retardation by Pectin", Science, 14, 1063–1064 (Nov. 20, 1964), birds were fed with food containing pectin that seemed to reduce the utilization of nutrients: the pectin-fed birds excreted three time as much liquid extract and almost twice as much cholesterol as did the control birds.

In the article, "Carrageenan as a Dietary Constituent for the Rat: Faecal Excretion, Nitrogen Absorption, and Growth", Canadian Journal of Biochemistry 43, 479–484, (1965), Hawkins and Yaphe studied the effect of carrageenan, which is a sulfated galactan extractable from certain red seaweeds, in the diet of young rats. The authors observed a slower growth rate in the rats caused by less absorption of dietary nitrogen.

The article "Treatment of Diabetes with Guar Gum", The Lancet, 779–780 (Oct. 15, 1977), describes a study of the effect of guar gum on normal diet of diabetic patients. The article concluded that unabsorbable carbohydrate of the guar type in the diet is useful in the treatment of diabetics.

The article "Effect of Pectin, Gum Arabic and Agar on Cholesterol Absorption, Synthesis, and Turnover in Rats", Journal of Nutrition 108(41), 630–639 (April, 1978), reports on a series of five experiments to determine the effect of pectin, gum arabic, and agar on cholesterol absorption, biosynthesis and turnover in rats. It was found that all three complex carbohydrates decreased cholesterol absorption and that protein had the greatest effect.

The article "Perfluorooctyl Bromide: A Potential Anti-Obesity Compound", Journal of Pharmaceutical Sciences 66(6), 907 (June, 1977), describes the use of perfluorooctyl bromide, a high molecular weight fluorocarbon used as a radiopaque contrast medium, to coat the stomach and intestines for forming a temporary barrier to the absorption of ingested food. There was a slight decrease in weight of the treated group of rats compared to a net increase in weight of the control group at the end of 14 days.

SUMMARY OF THE INVENTION

It is an object of the present invention to provide compositions for coating the small intestine of mammals to form a partial nutrient barrier on said intestine.

It is another object of the present invention to provide a method for weight control by the use of such nutrient barrier compositions.

In accordance with the present invention, weight control is achieved by controlling absorption of nutrients in the small intestine without significantly changing the eating habits of the individual. This is accomplished by forming a thin coating of a nutrient barrier composition on the inner surface of the intestine. The coating is effected by ingesting, prior to or along with the regular meals, a polymeric or other suitable film former capable of coating the small intestine and serving as a partial barrier against absorption of nutrients. The removal of the coating occurs as a result of the normal turnover of the cells, namely about 24 to 48 hours. Periodic repetition of coating over a period of time will result in a net loss of weight.

In order to achieve decreased absorption of nutrients, an effective coating is necessary that will adhere to the surfaces to be coated and will remain a barrier for a sufficient time period. It was observed that unless an effective compound is used for the coating, the amount necessary to achieve barrier properties is so large that the approach becomes impractical. Also, if actual binding does not take place between the intestinal surfaces and the coating, the effect of the coating on absorption rate of nutrients will be minimal.

To form an effective absorption barrier on the intestinal wall, several requirements must be met by the nutrient barrier composition. All the materials must be non-toxic and must not contain leechable or digestible components that would, in any way, deleteriously affect digestion, absorption or metabolism. The materials must be capable of forming a film or coating only in the pH range present in the small intestine, namely in the range of 5.5 to 8.5. The materials must not form a film or coating either in the stomach or in the large intestine in the pH range of 1.5 to 3.5, so not to interfere with the digestive and other phases of the nutritional process.

The objects of the present invention are achieved through the utilization of a composition comprising a polymeric material which is at least partially water soluble and contains ionizable groups, in combination with divalent metal ions which potentiate the effect of the polymeric material as a nutrient barrier when ingested.

DETAILED DESCRIPTION OF THE INVENTION

Broadly defined, the polymers discovered to be efficacious for the purposes of the present invention include certain anionic, cationic and neutral polymers.

I. Anionic Polymers

These polymers carry negative charges when in the ionized form. There is evidence in the literature that the anionic polymers bind to the cell surfaces and to protein molecules of the cells. The major forces responsible for these interactions are electrostatic in nature.

Suitable anionic polymers are represented by the generalized formulas:

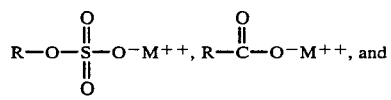

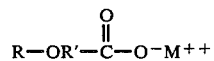

wherein R represents the polymeric chain or residue;

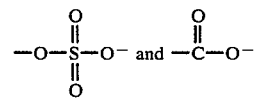

represent anionic ligands; and $M^{++}$ represents a divalent cation.

Specific anionic polymers useful in the present invention include:

A, sulfated polysaccharides;
B, carboxylated polysaccharides;
C, cellulose derivatives; and
D, sulfated, sulfonated or carboxylated synthetic polymers.

A. Sulfated Polysaccharides

Polysaccharides are polymeric carbohydrates which include sugars, cellulose, starch, and glycogen. All the polysaccharides are glycosides in which the acetal carbon atom of one monosaccharide unit is linked by way of an oxygen to one of the nonacetal carbon atoms of another monosaccharide, such as in:

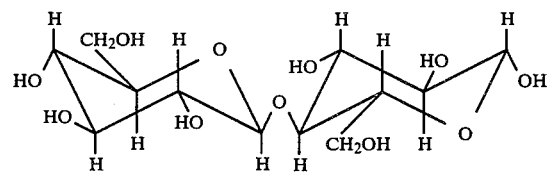

CELLOBIOSE (4-[β-glucosyl]-β-D-glucopyranose)

Sulfated sugar units in polysaccharides include 4-O-substituted D-galactopyranose and 2,6 disulphate residues, such as in carrageenan, which has the structural formula:

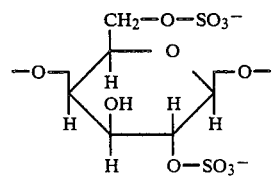

3-O-substituted N-acetyl-D-galactosamine; 4-sulfate residues as in chondroitin sulfate

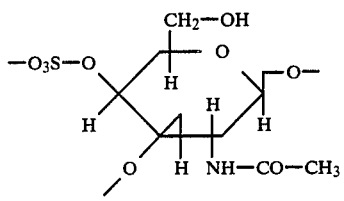

4-O substituted D-glucosamine residues as in heparin

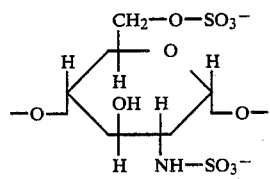

Sulfated esters of polysaccharides having the general formula:

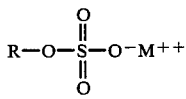

wherein, depending upon the specific polysaccharide, R consists of the following:

| Compound | R |
| --- | --- |
| kappa carrageenan | 3,6-anhydro-D-galactose linked through C-4 to D-galactose; |
| lambda carrageenan | α-D-galactose unites (1 → 3) linked; |
| iota carrageenan | D-galactose 3,6-anhydro-D-galactose; |
| Agar - Agar | D-galactose 3,6-anhydro-L-galactose; |
| Furcellaren | D-galactose 3,6-anhydro-D-galactose; |
| Laminaran sulfate | D-glucopyranose units linked through 1 and 3 positions by β-linkages; |
| Galactan sulfate | Galactan; and |
| Chondroitin sulfates | Galactosamino-glucuronans. |

The cation $M^{++}$ can be one of the following or a mixture of the following divalent metal ions: $Mg^{++}$, $Ca^{++}$, $Zn^{++}$, $Ba^{++}$.

B. Carboxylated Polysaccharides

Carboxylated polysaccharides are represented by the general formula

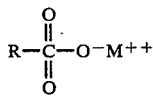

wherein R is as follows for various compounds:

| Compound | R |
| --- | --- |
| Pectin | D-galacturonoglycan in which the D-galactopyranosyluronic acid units are connected by (1→4) glycosidic linkages |
| Algin | anhydro-D-mannuronic acid and anhydro-L-guluronic acid residues |
| Gum karaya | complex polysaccharide; d-galacturonic acid, D-galactose, L-rhamnose |

The cation $M^{++}$ can be of the following or a mixture of the following divalent metal ions: $Mg^{++}$, $Ca^{++}$, $Zn^{++}$, $Ba^{++}$.

C. Cellulose Derivatives

These polysaccharides are derivatives of the naturally occurring polysaccharide, cellulose. Representative compounds are salts of alkyl cellulose sulfate, salts of acyl cellulose sulfate, and salts of carboxyalkyl cellulose having the following formulas respectively:

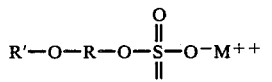

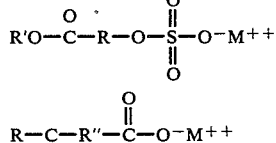

wherein:
R=anhydroglucose residue
$R'=CH_3$; $C_2H_5$; $C_3H_7$
$R''=CH_3$; $C_2H_5$;
$M^{++}=Mg^{++}$; $Ca^{++}$; $Zn^{++}$; $Ba^{++}$ Specific examples of these compounds are:
Sodium ethylcellulose sulfate;
Sodium cellulose acetate sulfate; and
Sodium carboxymethyl cellulose.

D. Sulfated, Sulfonated or Carboxylated Synthetic Polymers

These polymers may have aliphatic or aromatic backbones with sulfonate, sulfate or carboxyl groups attached according to the following general formulas respectively:

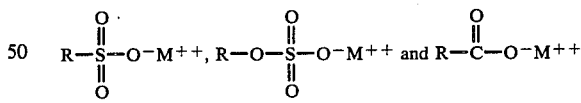

wherein R is an aliphatic or aromatic hydrocarbon chain such as polystyrene, poly(sulfone resin), or carboxylated (poly)vinyl, and $M^{++}$ is $Mg^{++}$, $Ca^{++}$, $Zn^{++}$, or $Ba^{++}$.

II. Cationic Polymers

These polymers carry positive charges when in the ionized form. Aminopolysaccharides are representative of this group of polymers. These polymers are mainly of animal origin which contain units of amino sugars, most frequently D-glucosamine (2-amino-2-deoxy-D-galactose).

Representative compounds of this class have the general formula of:

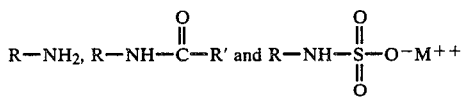

wherein R is a sugar residue, R' is $CH_3$ or $C_2H_5$, and $M^{++}$ is $Mg^{++}$, $Ca^{++}$, $Zn^{++}$ or $Ba^{++}$.

Specific examples of such compounds are: Chondroitin Sulfates which can be characterized as being both anionic and cationic due to the electrostatic charges present), Dermatan Sulfate, Keratosulfate, Hyaluronic Acid, Heparin, and Chitin.

III. Neutral Polymers

Neutral polymers effective in the practice of the present invention are those which include atoms having polarizable electrons, such as oxygen, nitrogen, sulfur, fluoride, chloride, bromide, iodide. In the presence of a cation such as $Ca^{++}$, $Mg^{++}$, $Zn^{++}$, and $Ba^{++}$, these polymers are partially polarized, thus giving rise to the intermolecular interactions between the polymer and the protein molecules of the intestinal surface.

Representative polymers include:

A. Polysaccharides

Examples: Starch, Glycogen, Glucan, Fructans, Mannans, Galactomannas, Glucomannans, Galactans Abrabinans, Xylans, Glycuranans, Guar Gum, Locust Bean Gum, Dextran, Starch Amylose, and Starch Amylopectin.

B. Cellulose Derivatives

Examples: Methylcellulose, Hydroxyethylcellulose, Ethylhydroxyethyl cellulose, Hydroxpropyl cellulose.

C. Synthetic Polymers

Examples: Polyvinylpyrrolidone, Polyvinyl alcohol, and Ethylene oxide polymers.

TESTING EFFICACY OF THE INVENTION

The effectiveness of the anti-obesity formulations was determined by in vitro and in vivo test methods. The in vitro method utilizes a segment of intestine excised from an experimental animal. The physiological activity of the intestinal mucosa depends on continuous supply of oxygen and nutrients to the intestinal cells. Therefore, once the intestine is excised from the experimental animal, it is maintained in a continuously oxygenated Ringer's solution.

The experimental animals used in this test were male rats (Charles River) weighing 300–350 g each. Each rat was fasted for 24 hours prior to the test. About a 50 cm section of the small intestine leading from the stomach and extending into the large intestine was excised and placed into 25 ml of preoxygenated Ringer's solution. Omitting the first 10 cm measured from the end leading from the stomach, a 10 cm test segment was taken. This was perfused with 10 ml of Ringer's solution, weighed, and then cannulated at both ends and mounted on a test apparatus.

The test apparatus consisted of two cuvettes, one of which contained an "inside" solution while the other contained an "outside" solution. The inside solution consisted of 25 ml of 5 mM glucose in Ringer's solution and 0.1 ml of a solution of glucose $DL^{14}C$ having 0.5 uCi activity. The outside solution consisted of 25 ml of the Ringer's solution. The two cuvettes were connected via a pair of capillary tubes, the ends of which were immersed into the respective solutions. The 10 cm segment of the intestine to be tested was mounted on the ends of the capillary tubes and completely immersed in the cuvette containing the outside solution.

The test consisted of perfusing the inside solution through the intestine for 30 minutes at a flow rate of about 3 ml per minute at a temperature of 37° C. The rate of transport of glucose from the inside (mucosal side) to the outside (serosal side) of the intestine was determined from the change in the concentration of the glucose in these two solutions. The concentration changes were determined by sampling 5 ml of the inside and 5 ml of the outside solutions, adding 5 ml INSTA-GEL scintillations cocktail to each, and counting the number of disintegrations per minute using Beckman LS-330 Liquid Scintillation Counter. This procedure was repeated three times.

The rate of glucose transport from inside to outside of the intestine was determined by comparing the cumulative disintegration counts in the inside and in the outside solutions. The change in the slope of the count versus time plot from the second to the third run was compared for the control and for the active compounds. The magnitude of the change from the control gives the effectiveness of the compound being tested.

The following examples are presented to illustrate the compositions prepared in accordance with the present invention, but are not intended to limit the scope thereof.

EXAMPLE 1

A one percent solution of sodium carrageenan (D-galactose-4-sulfate 3,6-anhydro-D-galactose) in distilled water was perfused through the intestine for 10 minutes. The intestine was washed by perfusing Ringer's Solution through it for 10 minutes and then tested for rate of transport of $^{14}C$-Glucose. It was determined that the rate of transport of $^{14}C$-Glucose is 49% higher (+49%) than the precoating rate of transport. Since this is close to the result obtained for the control where the intestine is perfused with Ringer's Solution in place of the polymer solution, the sodium carrageenan alone is not an effective nutrient barrier compound.

When the same experiment is repeated with a fresh intestine and with a coating solution containing 1% sodium carrageenan and 1% calcium lactate, the $^{14}C$-Glucose rate of transport is 32% lower (−32%) than the precoating rate. As can be readily ascertained, the combination of sodium carrageenan with calcium ion is an effective nutrient barrier.

EXAMPLE 2

The procedure of Example 1 is repeated using a 1% solution of Gelcarin-HMR (D-galactose-4-sulfate-3,6-anhydro-D-galactose) which includes 0.170 mol % $Ca^{++}$ as the nutrient barrier composition. The rate of glucose transport is determined to be −36% of the precoating rate of transport.

When a fresh solution of 1% Gelcarin-HMR and 1% calcium lactate is perfused through the intestine, the rate of glucose transport is −43% of the precoating rate of transport.

When 3% calcium lactate is added to the coating solution of 1% Gelcarin-HMR, the rate of glucose transport is −27% of the precoating rate of glucose transport.

EXAMPLE 3

This example illustrates that a synthetic polymer having sulfonic acid groups is not effective when the counter ions are monovalent cations such as $Na^+$, $K^+$, but the same polymer becomes effective when divalent cations such as $Ca^{++}$ are added to the solution. Commercially available sulfonated polymers and monomers may therefore be converted into effective coating agents by adding a divalent cation to their solutions.

| Polymer Solution | Gm-mols per 100 gm Polymer | | | % Change glucose transport |
|---|---|---|---|---|
| | $Na^+$ | $K^+$ | $Ca^{++}$ | |
| 1% Polysulfone resin sodium sulfonate | 0.334 | — | — | +35 |
| 1% Polysulfone resin sodium +1% Calcium lactate | 0.334 | — | 0.324 | −61 |
| 1% Parastyrene sulfonic acid K Salt | — | 0.209 | — | +73 |
| 1% Parastyrene sulfonic acid +1% Calcium lactate | — | 0.209 | 0.324 | −9 |
| 1% Polystyrene sulfonic acid (MW40000)Na Salt | 0.334 | — | — | +51 |
| 1% Polystyrene sulfonic acid +1% Calcium lactate | 0.334 | — | 0.324 | −47 |
| 1% Polystyrene sulfonic acid (MW5000,000)Na Salt | 0.291 | — | — | +59 |
| 1% Polystyrene sulfonic acid +1% Calcium lactate | 0.291 | — | 0.324 | −56 |
| 1% Polystyrene sulfonic acid (3,000,000)Na Salt | 0.263 | — | — | +61 |
| 1% Polystyrene sulfonic acid +1% Calcium lactate | 0.263 | — | 0.324 | −7 |

The above studies also show that the monomer and the very high molecular weight polymer is not as effective as the intermediate molecular weight polymers. However, the effectiveness of all the compounds increased significantly as a result of the addition of calcium lactate to the coating solution.

EXAMPLE 4

This example illustrates that a solution of a cellulose derivative polyanion such as sodium ethylcellulose sulfate is rendered very effective as a nutrient barrier by the addition of a divalent cation.

| Polymer Solution | Gm-mols per 100 gm Polymer | | % Change glucose transport |
|---|---|---|---|
| | $Na^+$ | $Ca^{++}$ | |
| 1% Sodium Ethylcellulose Sulfate | 0.170 | — | +6 |
| 1% Sodium Ethylcellulose Sulfate +1% Calcium lactate | 0.170 | 0.324 | −45 |

EXAMPLE 5

This example illustrates that the polycarboxylic acids become effective after calcium is added to the solution whereas the polymer solution by itself is not effective.

One percent Pectin-NF solution in distilled water is perfused through the intestine. The rate of glucose transport was +75% higher than the precoating rate of glucose transport.

When a coating solution containing 1% pectin and 1% calcium lactate is perfused through the intestine the rate of glucose transport is reduced by −35% of the precoating rate of glucose transport. Therefore, a polycarboxylic acid which by itself is not an effective coating agent has been rendered effective by the addition of a divalent cation i.e. calcium.

EXAMPLE 6

This example illustrates that the effect shown in Example 6 is not attributable to the substrate itself to which the carboxyls are chemically bonded, but it is attributable to the carboxyl groups.

Tragacanth-C which is a mixture of the salt of the complex acid polysaccharide, a neutral polysaccharide, and a small amount of glycoside is used in this study. After 1% solution of Tragacanth-C is perfused through the intestine the rate of glucose transport increases by +38% of the precoating rate i.e. 38% higher than the precoating rate. Since this value is close to the value obtained for the control, Tragacanth-C is not effective.

When a solution containing 1% Tragacanth-C along with 1% calcium lactate is used as the coating solution, the rate of glucose transport is −56% lower than the precoating rate. Therefore, Tragacanth-C along with $Ca^{++}$ is very effective in coating the intestine and in reducing the glucose transfer rate.

EXAMPLE 7

This example illustrates that polymers which are nonionic but have groups or atoms with polarizable electrons such as R-OH are also effective coating agents when combined with divalent cations.

After 1% solution of hydroxypropyl cellulose (Klucel$^R$ −NF) is perfused through the intestine, it is observed that the rate of glucose transport increases to +71% above the precoating rate; when on the other hand the coating solution is of 1% calcium lactate and 1% hydroxypropyl cellulose, the rate of glucose transport decreases to −24% below the precoating rate.

EXAMPLE 8

A 1% solution of polyvinylpyrrolidinone (MW40,000) was used as the coating solution. The rate of glucose transport increased to +33% above the precoating rate of glucose transport. When 1% calcium lactate was added to the 1% polyvinylpyrrolidinone solution, the rate of glucose transport was reduced to −38% of the precoating rate.

EXAMPLE 9

This example illustrates that the effect observed by adding calcium lactate to the coating solution of the preceding examples is not due to the calcium lactate alone. When a 1% to 3% solution of calcium lactate alone is used as the coating solution, the rate of glucose transport increased to about +40% above the precoating rate. Therefore, calcium lactate alone is not an effective coating agent.

EXAMPLE 10

This example illustrates, that the intestinal coating achieved by perfusing a solution of nutrient barrier composition through the intestine not only reduces the rate of glucose transport in the intestine, but also reduces the rate of transport of other nutrients such as L-Methionine. The results are summarized below:

| Coating solution | % Change in rate of transport of L-methionine |
|---|---|
| Control-Ringer Solution | +115% |

-continued

| Coating solution | % Change in rate of transport of L-methionine |
|---|---|
| 1% Gelcarin-HMR | −6% |
| 1% Gelcarin-HMR +1% Calcium lactate | −30% |
| 1% Polystyrene sulfonic acid (MR500,000) +1% Calcium lactate | −31% |

EXAMPLE 11

This example illustrates the effect of another divalent cation, $Zn^{++}$, on the effectiveness of sodium carrageenan as a nutrient barrier composition.

A 1% sodium carrageenan solution alone resulted in a +61% rate of transport of L-Methionine. A solution of 1% sodium carrageenan and 1% $ZnCl_2$ reduced the rate of +27%.

EXAMPLE 12

This example illustrates the effect of the ratio of negatively charged ions to $Ca^{++}$ ion on the effectiveness of sodium carrageenan as a nutrient barrier for glucose transport.

| Coating solution | % calcium lactate | O Ca++ | % Change in rate glu. transport |
|---|---|---|---|
| 1% Sodium Carrageenan | 0 | 35.4 | +69 |
| 1% Sodium Carrageenan | 0.1 | 7.7 | +80 |
| 1% Sodium Carrageenan | 0.2 | 4.3 | +10 |
| 1% Sodium Carrageenan | 0.5 | 1.9 | +32 |
| 1% Sodium Carrageenan | 1.0 | 0.96 | −45 |

As the data show, the ratio of $Ca^{++}$ to O is preferably at least 0.5 to 1 to effectively inhibit glucose transport, although lower ratios of 0.2 to 1 are significantly more effective than sodium carrageenan alone.

The following examples are based on the so-called "surviving in vitro" test method following in vivo intestinal coating. Briefly, this is a modification of the method used in Examples 1 through 12. In this test, the nutrient barrier composition is dissolved in water and administered to the test animals prior to feeding or along with the food. The viscosity of the solution should be in the range of about 50 to 250,000 and preferably in the range of 20,000 to 90,000 cps. as determined using a Brookfield viscometer.

The advantage of the in vivo method lies in the fact that the intestinal coating is done in vivo which may better simulate the method of actual use. The disadvantage of the method is that each intestinal segment can be tested only once, so each control test and the treatment formulation test must be on a different animal. Thus, the normal variations between the individual animals contribute to the differences that are measured. In this method, a rat was fasted for 24 hours, then intubated with 5 ml of a solution of a barrier composition polymer plus calcium lactate using a stomach intubation tube. The rat was put back in its cage for 1–6 hours depending upon the lead time or stomach emptying time desired. The animal was then sacrificed and intestine excised and preserved in preoxygenated Ringer's Solution. A 10 cm segment of the intestine was obtained as specified in the previous test and mounted on the same test equipment. The test was run continuously for 180 minutes by perfusing $^{14}C$ labelled glucose or $^{14}C$ labelled L-Methionine solution through the intestine. The inside and outside solutions were sampled every 10–30 minutes and the amount of the radioactive glucose in each sample determined by scintillation counting.

The labelled glucose concentration in the inside and outside solutions was established as a function of time, and the amount of glucose transported from inside the intestine to the outside was expressed as the percentage of the inside concentration. These percentages were compared to control animals and the difference between the control and the treatment groups is expressed as percent change from the control.

For the control study, each of three rats were intubated with 5 ml of water. A lead time (hereinafter denoting the time between intubation and the time of sacrifice) of one hour was allowed. After sacrifice, the percent transport of glucose was determined as follows:

| | Glucose Transported | | |
|---|---|---|---|
| | 60 min. | 120 min. | 180 min. |
| control (1) | 0.3903 | 1.2689 | 2.8291 |
| control (2) | 0.2697 | 0.7985 | 1.7303 |
| control (3) | 0.3671 | 0.8835 | 2.6784 |
| Avg. | 0.3424 | 0.9836 | 2.4126 |
| SD | 0.064 | 0.251 | 0.596 |

EXAMPLE 13

Each of two rats were intubated with 5 ml of a 6.5% GELCARIN-HMR solution. A lead time of one hour was allowed before sacrifice. At sacrifice one of the rats had 1 ml of the solution still remaining in the stomach. The % transport of glucose and comparison with the control study were as follows:

| % Glucose transported | | | % Reduction in glucose transport from control | | |
|---|---|---|---|---|---|
| 60 min. | 120 min. | 180 min. | 60 min. | 120 min. | 180 min. |
| 0.1075 | 0.2876 | 0.4655 | | | |
| 0.0830 | 0.2589 | 0.9418 | | | |
| AVG 0.0952 | 0.2733 | 0.7036 | −72.2 | −72.2 | −70.8 |

EXAMPLE 14

One rat was intubated with 10 ml of a 6.5% Gelcarin-HMR solution. A lead time of one hour was allowed before sacrifice. At sacrifice the rat had 3 ml of the solution still remaining in the stomach. The % transport of glucose and comparison with control study were as follows:

| % Glucose transported | | | % Reduction in glucose transport from control | | |
|---|---|---|---|---|---|
| 60 min. | 120 min. | 180 min. | 60 min. | 120 min. | 180 min. |
| 0.04650 | 0.1607 | 0.8459 | −86.4 | −83.7 | −64.9 |

EXAMPLE 15

One rat was intubated with 2.5 ml of a 6.5% Gelcarin-HMR solution. A lead time of one hour was allowed before sacrifice. At sacrifice the rat had 1 ml of the solution still remaining in the stomach. The % transport of glucose and comparison with the control study were as follows:

| % Glucose transported | | | % Reduction in glucose transport from control | | |
|---|---|---|---|---|---|
| 60 min. | 120 min. | 180 min. | 60 min. | 120 min. | 180 min. |
| 0.1819 | 0.6359 | 1.4328 | −46.9 | −35.3 | −40.6 |

EXAMPLE 16

One rat was intubated with 5 ml of a 3.0% Gelcarin-HMR solution. A lead time of one hour was allowed before sacrifice. At sacrifice the rat had no solution remaining in the stomach. The % transport of glucose and comparison with the control study were determined as follows:

| % Glucose transported | | | % Reduction in glucose transport from control | | |
|---|---|---|---|---|---|
| 60 min. | 120 min. | 180 min. | 60 min. | 120 min. | 180 min. |
| 0.09877 | 0.3882 | 1.2090 | −71.2 | −60.5 | −49.9 |

EXAMPLE 17

One rat was intubated with 5 ml of 1.0% Gelcarin-HMR solution. A lead time of one hour was allowed before sacrifice. At sacrifice the rat had no solution remaining in the stomach. The % transport of glucose and comparison with the control study were determined as follows:

| % Glucose transported | | | % Reduction in glucose transport from control | | |
|---|---|---|---|---|---|
| 60 min. | 120 min. | 180 min. | 60 min. | 120 min. | 180 min. |
| 0.3098 | 1.7082 | 5.7549 | −9.5 | +73.5 | +138.5 |

The 5 ml of 1.0% Gelcarin-HMR solution did not reduce the rate of glucose transport.

EXAMPLE 18

One rat was intubated with 5 ml of a 6.5% Gelcarin-HMR solution. A lead time of one hour was allowed before sacrifice. At sacrifice that rat had 1 ml of solution remaining in the stomach. The % transport of L-Methionine and comparison with the control study were as follows:

| % L-Methionine transported | | | | % Reduction in L-Methionine transport from control | | | |
|---|---|---|---|---|---|---|---|
| 30 min. | 60 min. | 90 min. | 120 min. | 30 min. | 60 min. | 90 min. | 120 min. |
| 0.006817 | 0.06276 | 0.13806 | 0.26988 | −94.0 | −82.4 | −84.8 | −84.1 |

EXAMPLE 19

One rat was intubated with 5 ml of a 2.5% Gelcarin-HMR solution. A lead time of one hour was allowed before sacrifice. At sacrifice the rat had no solution remaining in the stomach. The % transport of L-Methionine and comparison with the control stude were determined as follows:

| % L-Methionine transported | | | | % Reduction in L-Methionine transport from control | | | |
|---|---|---|---|---|---|---|---|
| 30 min. | 60 min. | 90 min. | 120 min. | 30 min. | 60 min. | 90 min. | 120 min. |
| 0.05057 | 0.2248 | 0.5509 | 0.9425 | −55.6 | −37.0 | −39.5 | −44.6 |

To determine the performance of the nutrient barrier compositions of the present invention, in vivo intubation weight gain tests were also run as follows. The experimental rats were acclimated to eat for 3 hours a day only, but they had unlimited access to water. Body weight changes and food consumption were measured daily. After body weight changes and food consumption had stabilized, the animals were divided into treatment and control groups.

Test materials, including the controlled (distilled water) were administered into the stomach of the rats using a 10 ml syringe fitted with a No. 8 French catheter. The body weight of the rats were determined every other day before intubation. Food consumed by each animal was determined daily. Examples 20 and 21 are based on this test.

EXAMPLE 20

Three groups of rats, 4 in each group, after acclimation and stabilization of their weights, were intubated with 5 ml of solutions as follows:

Group I with 5.0% Anionic Carboxymethylcellulose,
Group II with 6.5% Gelcarin-HMR, and
Group III with distilled water.

The animals were fed daily as described above. The results obtained are shown in Table I.

TABLE 1

| | Average weight initial gms. | Food consumed/ day/rat (average) | Weight Gain Average wt. increased | | |
|---|---|---|---|---|---|
| | | | 2 wks. | 3 wks. | 4 wks. |
| Group I | 188 | 17.8 gms. | 19.3 | 35.1 | 33.5 |
| Group II | 181 | 14.7 gms. | 15.5 | 26.0 | 29.8 |
| Group III | 169 | 17.5 gms. | 24.6 | 43.2 | 50.3 |

EXAMPLE 21

In a one month study, a group of 5 adult rats were intubated with 5 ml of a formulation containing 1% Gelcarin-DG and 1% calcium lactate in water. Another group of 6 adult rats served as the control and these were intubated with 5 ml of water instead of the formulation. The following results were obtained.

| | Control group | Treated group |
|---|---|---|
| Initial Average Body Weight | 222.7 gms | 232.2 gms |
| Final (one month later) Body Wt. | 244.8 gms | 238.2 gms |
| Percent Body Weight Gain | 9.9 | 2.6 |
| Food Consumed | 341.0 gms | 338.6 gms |
| Weight Gain per 100 gm Food | 4.9 | 1.8 |

This data shows that the rats on the placebo formulation gained about 2.7 times more weight per 100 gms. food consumed as compared to the rats on the carrageenan formulation.

EXAMPLE 22

This study was conducted to determine if the anti-obesity formulation can be administered in dry form and whether it is effective in this form. The following diets were fed ad libitum to the four groups of rats, 10 in each group:

| Rat | Formulation |
| --- | --- |
| Group A | 10% Gelcarin-HMR + 90% Purina Chow |
| Group B | Control - 100% Purina Chow |
| Group C | 10% Gelcarin-HMR + 1% Calcium Lactate + 89% Purina Chow |
| Group D | 10% Pectin-NF + 90% Purina Chow |

The Purina Chow was Rodent Laboratory Chow ® 5001 which is in ground form. This is blended with the Gelcarin-HMR or with Pectin-NF in a V-blender. Food and water were constantly available to the animals. Food consumptions were recorded daily and body weights were recorded twice a week. Result and statistical comparison are shown in Table II.

TABLE II

Statistical Comparisons* of Rats Fed Dry Diet Formulations A, B, C & D

| Group | Average Body Weight, g Initial | Average Body Weight, g Final | Average Weight Gain, g | Food Efficiency** Weight Gained g/100 g Food | Total Avg. Food** Consumed/Rat g/Kg |
| --- | --- | --- | --- | --- | --- |
| A | 162.9 ± 9.8 | 395.4 ± 36.9 | 232.5 ± 33.4 | 17.70 ± 1.475 | 5112 ± 226 |
| B | 157.6 ± 8.4 | 425.6 ± 27.4 | 268.0 ± 25.7 | 19.17 ± 1.084 | 5290 ± 162 |
| C | 160.9 ± 7.9 | 408.0 ± 34.9 | 237.1 ± 27.4 | 17.96 ± 1.791 | 5150 ± 276 |
| D | 157.2 ± 6.0 | 404.9 ± 43.3 | 247.7 ± 39.4 | 19.02 ± 2.010 | 5048 ± 226 |

*Compared by 1-Way analysis of Variance. Values shown are means ± Standard Deviation.
**Food values adjusted to reflect the amount of actual food in total diet.

According to the foregoing invention, formulations for human consumption were prepared. Formulations for human consumption must be palatable. The following two examples illustrate acceptable formulations that were tested by human volunteers. The ingredients, other than water, were blended first, then water was added with high speed stirring using a Lightnin' Mixer.

EXAMPLE 23

| | Amount |
| --- | --- |
| Carrageenan-HMR | 9.0 gms |
| Tangerine Flavor No. 6037-8-5 oz (SunKist) | 0.4 gms |
| Orange Flavor No. 6004-8-563 | 0.4 gms |
| Citric Acid[1] | 0.3 gms |
| Vanilla S-18301 13 drops[2] | 0.25 gms |
| Sugar Twin Sugar Replacement | 2.25 gms |
| USP Saccharin Mollinckrott Lot CRT | 0.02 gms |
| | 12.620 gms |
| Water | 287.38 gms |
| TOTAL | 300.00 gms |

[1]J. T. Baker Lot No. 44551
[2]Using medicine dropper

EXAMPLE 24

| | Amount |
| --- | --- |
| FDC Red #40 | 0.06 gms |
| FDC Yellow #5 | 0.06 gms |
| Gelcarin HMR-Marine Colloid Lot 303118 | 4.00 gms |
| Citric Acid-J. T. Baker Lot 44551 | 0.35 gms |
| Tangerine Flavor-SunKist #6037-8-502 | 0.40 gms |
| Orange Flavor-SunKist #6004-8-563 | 0.40 gms |
| Sugar Twin Sugar Replacement | 1.85 gms |
| Saccharin-Mollinckrott Lot CRT | 0.05 gms |
| Food Vanilla-FMC 5-18301 12 drops | 0.30 gms |
| Tap Water | 192.53 gms |
| TOTAL | 200.00 gms |

In preparing the various anti-obesity formulations of the present invention for both in vitro and in vitro tests the viscosities were determined as follows: the specified amount of the film-forming or coating ingredients was weighed into distilled water to make-up the desired concentration and the mixture was stirred until a uniform solution or paste was obtained. Viscosity was determined using a Brookfield viscometer. Typical viscosities for various coating materials and concentrations are shown in Table III.

TABLE III

| Solution | Viscosity in cps. |
| --- | --- |
| 1% Gelcarin-HMR | 200 |
| 3.5% Gelcarin-HMR | 22,000 |
| 6.5% Gelcarin-HMR | 86,000 |
| 1% Gelcarin DG | 16,000 |
| 2% Gelcarin DG | 60,000 |
| 2.5% Gelcarin DG | 86,000 |
| 3% Gelcarin DG | 141,000 |
| 4% Gelcarin DG | 230,500 |
| 1% Gelcarin DG + 1% Ca lactate | 5,000 |
| 3.5% Gelcarin DG + 3.5% Ca lactate | 48,000 |
| 3.5% Viscarin | 41,000 |
| 3.5% Viscarin Ba$^{++}$ | 38,000 |
| 3.5% Viscarin Ca$^{++}$ | 42,000 |
| 4% Viscarin | 80,000 |
| 3.5% Viscarin + 3.5% Ca lactate | 76,000 |
| 1% Klucel | 1,200 |
| 2% Klucel | 20,000 |
| 2% Pectin | 280 |
| 3% Pectin | 1,150 |
| 3.5% Pectin | 1,800 |
| 4% Pectin | 4,100 |
| 5% Pectin | 13,500 |
| 3.5% Polystyrene sulfonic acid | 250 |
| 3.5% Starch H-50B | 1,700 |
| 3.5% Starch 36,46:5 | 1,500 |
| 3.5% Chondroitin Sulfate "C" | 50 |

Dose levels for human consumption of the anti-obesity formulations may be established by extrapolating the in vitro dose levels obtained on rats to 70 kg person body weight—metabolic weight relationships as described by Kleiber, Max in "The Fire of Life", John Wiley & Sons, Inc., 1961.

| | Rat | Human |
| --- | --- | --- |
| Higher Dose Level | | |
| Body Weight | 0.232 kgs | 70.0 kgs |

|  | Rat | Human |
| --- | --- | --- |
| Metabolic body weight | 0.334 kgs | 24.2 kgs |
| Dose needed per administration | 0.050 gms | 3.62 gms |
| This amount (9.3 gms) as a 3.5% solution is equal to 265.7 mls or 9 oz. | | |
| Lower Dose Level | | |
| Body weight | 0.232 kgs | 70.0 kgs |
| Metabolic body weight | 0.334 kgs | 24.2 kgs |
| Dose needed per administration | 0.050 gms | 3.62 gms |
| This amount (3.62 gms) as a 3.5% solution is 103.4 mls or 3.5 oz. | | |

Upon ingestion of the anti-obesity formulation of the present invention, an effective coating is formed on the small intestine which has a pH of about 7.5, while the coating of the stomach is minimal due to its pH which ranges from about 1.5 to about 2.5. This is desirable since the minimal coating of the stomach will not interfere with the digestive function of the stomach while in the intestine the coating of same will result in a reduced rate of nutrient absorption and ultimately in loss of undesirable weight.

The affect of the pH environment of the stomach and the small intestine is shown in the following tow examples which are based on the in vitro method used in Examples 1-12.

EXAMPLE 25

When a 1% Gelcarin-HMR solution was used as the coating solution of which the pH was 9.92, the rate of glucose transport compared to the control was lowered by about −36%. When the pH of this solution was adjusted to 2.45, using HCl(IM), the reduction in the rate of glucose transport was +10.7.

To determine whether the process of film forming may be reversed, the pH of 2.45 was re-adjusted, using NaOH (IM) to 9.83. As a result, the reduction in the rate of glucose transport increased to −0.6%.

EXAMPLE 26

The same procedure was used as in Example 25 except instead of using NaOH to readjust the pH to 9.83, Ca(OH)$_2$ was used. The reduction in the rate of glucose transport was −18.5% due to the presence of divalent calcium cations which advantageously influence the binding of the film to the cells of the intestines.

The presence of calcium containing food, such as milk for example, in the digestive system would have a similarly beneficial effect on film formulation and adherence of same to the cells of the small intestine.

It should be understood by those skilled in the art that, while the invention has been described and illustrated above in connection with certain specific embodiments, many variations and modifications may be employed without departing from the scope of the invention.

What is claimed is:

1. An oral composition of matter for coating the small intestine of a mammal comprising: a polymeric material that is capable of forming a nutrient barrier in the pH environment of 5.5 to 8.5 of the small intestine, said polymeric material having atoms containing polarizable electrons thereon, said atoms being selected from the group consisting of oxygen, nitrogen, sulfur in combination with a divalent cation said divalent cation is selected from the group consisting of Ca$^{++}$, Mg$^{++}$, Zn$^{++}$ and Ba$^{++}$ wherein the ratio of said atom containing polarizable electrons thereon to said divalent cation is in the range of 7.7 to 1 or <1 in a pharmaceutically acceptable carrier.

2. The composition of claim 1 wherein said pharmaceutically acceptable carrier is a liquid.

3. The composition of claim 1 wherein said pharmaceutically acceptable carrier is a solid.

4. The composition of claim 1 wherein the polymeric material is an anionic carboxylated polysaccharide having the formula

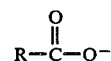

wherein R=pectin: D-galacturonoglycan in which the D-galactopyranosyluronic acid units are connected by (1→4) glycosidic linkages; algin: anhydro-D-mannuronic acid and anhydro-L-guluronic acid residues; or gum karaya: D-galacturonic acid, D-galactose and L-rhamnose.

5. The composition of claim 1 wherein the polymeric material is an anionic cellulose derivative having the formulae

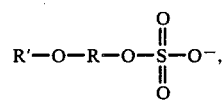

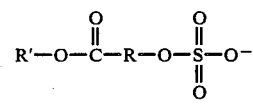

and

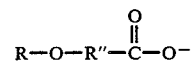

where R=anhydroglucose residue; R'=CH$_3$, C$_2$H$_5$, or C$_3$H$_7$; R''=CH$_3$, or C$_2$H$_5$.

6. The composition of claim 5 wherein said anionic cellulose derivative is sodium ethylcellulose sulfate.

7. The composition of claim 5 wherein said anionic cellulose derivative is sodium cellulose acetate sulfate.

8. The composition of claim 5 wherein said anionic cellulose derivative is carboxymethyl cellulose.

9. The composition of claim 1 wherein the polymeric material is an anionic sulfated synthetic polymer having the formula

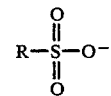

wherein R=(poly)alkyl or (poly)aryl sulfone.

10. The composition of claim 1 wherein the polymeric material is an anionic sulfonated synthetic polymer having the formula

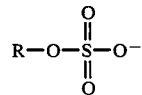

wherein R=(poly)styrene; (poly)alkyl or (poly)aryl sulfone resin.

11. The composition of claim 1 wherein the polymeric material is an anionic carboxylated synthetic polymer having the formula

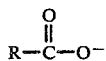

wherein R-poly(vinyl carboxylate).

12. The composition of claim 1 wherein the polymeric material is a cationic aminopolysaccharide having the formula

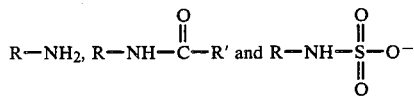

wherein R=an anhydroglucose unit and R'=CH$_3$, or C$_2$H$_5$.

13. The composition of claim 12 wherein the aminopolysaccharide is chondroitin sulfate.

14. The composition of claim 12 wherein the aminopolysaccharide is dermatan sulfate.

15. The composition of claim 12 wherein the aminopolysaccharide is keratosulfate.

16. The composition of claim 12 wherein the aminopolysaccharide is hyaluronic acid.

17. The composition of claim 12 wherein the aminopolysaccharide is heparin.

18. The composition of claim 12 wherein the aminopolysaccharide is chitin.

19. The composition of claim 1 wherein the polymeric material is neutral synthetic polymer selected from the group consisting of polyvinylpyrrolidone, polyvinyl alcohol or polyethylene oxide.

20. A method of reducing the amount of nutrient absorption in the small intestine of a mammal by administering to said mammal an effective amount of the composition of claim 1.

21. The method of claim 20 wherein said composition is administered to said mammal prior to feeding.

22. The method of claim 20 wherein said composition is administered to said mammal along with feeding.

* * * * *